United States Patent [19]

Lewis et al.

[11] Patent Number: 5,587,323
[45] Date of Patent: Dec. 24, 1996

[54] MECONIUM ASSAY PROCEDURE

[75] Inventors: Douglas E. Lewis, Oak Brook; Christine M. Moore, Forest Park, both of Ill.

[73] Assignee: United States Drug Testing Laboratories, Inc., Chicago, Ill.

[21] Appl. No.: 433,232

[22] Filed: May 2, 1995

[51] Int. Cl.$^6$ ........................................ G01N 1/18
[52] U.S. Cl. .................. 436/178; 436/92; 436/98; 436/161; 436/174; 436/177; 436/816; 436/901; 73/61.52; 73/61.53; 73/61.55; 210/635; 210/656; 210/660; 210/198.2
[58] Field of Search .................. 436/92, 93, 98, 436/174, 175, 177, 178, 816, 901, 161; 73/61.52, 61.53, 61.55; 210/635, 656, 198.2, 660, 661, 679, 690, 691, 692

[56] References Cited

U.S. PATENT DOCUMENTS

| | | | |
|---|---|---|---|
| 4,771,005 | 9/1988 | Spiro | 436/93 |
| 5,015,589 | 5/1991 | Ostrea, Jr. | 436/92 |
| 5,185,267 | 2/1993 | Ostrea, Jr. | 436/92 |
| 5,326,708 | 7/1994 | Lewis | 436/92 |
| 5,532,131 | 7/1996 | Lewis | 435/7.9 |

OTHER PUBLICATIONS

Browne et al. *Journal of Chromatography–Biomedical Applications*, vol. 575, 1992, pp. 158–161.

Murphey et al. *Journal of Chromatography–Biomedical Applications*, vol. 613, 1993, pp. 330–335.

Mahone et al. *American Journal of Obstetrics & Gynecology*, vol. 171, No. 2, Aug. 1994, pp. 465–469.

Lewis et al. *Clinical Toxicology*, vol. 32 (6), 1994, pp. 697–703.

Ostrea et al. *The Journal of Pediatrics*, vol. 122, No. 1, Jan. 1993, pp. 152–154.

*Primary Examiner*—Jill Warden
*Assistant Examiner*—Maureen M. Wallenhorst
*Attorney, Agent, or Firm*—Hill, Steadman & Simpson

[57] ABSTRACT

A improved method for preparing a concentrated meconium extract containing basic and acid-neutral target analytes present in a meconium sample suspected of containing the target analytes is provided. The meconium sample is extracted with a mixed solvent of acetonitrile and a volatile organic acid and the resulting organic phase is separated. The organic phase is diluted with water to provide an organic solution which is passed through a mixed mode solid phase extraction column having strong cation exchange and hydrophobic functionality. Acid-neutral and basic target analytes are sequentially eluted from the column and the eluates are combined to form a combined extract. The combined extract is evaporated to dryness and reconstituted in buffer to provide a clean concentrated neonatal meconium extract for use in qualitative and quantitative analyses.

1 Claim, No Drawings

MECONIUM ASSAY PROCEDURE

BACKGROUND OF THE INVENTION

The present invention generally relates to drug testing methods for determining maternal drug use during pregnancy and fetal exposure to drugs in utero. More particularly, it relates to a new and improved method for extracting drug of abuse analytes from meconium to provide a concentrated meconium extract for use in immunoassay screening procedures and quantitative determinations.

In U.S. Pat. No. 5,326,708, granted Jul. 5, 1994, a new and improved method for obtaining non-aqueous concentrated cocktail meconium extracts containing substantially all of any drugs of abuse target analytes present in a meconium sample was described. The method described in this patent demonstrated that an organic extraction procedure yielded a dramatically improved sensitivity in comparison with earlier aqueous-based and methanol-based extraction methods.

The present invention provides an improvement over the invention described in U.S. Pat. No. 5,326,708.

SUMMARY OF THE INVENTION

In accordance with the present invention, a new and improved method of making a concentrated neonatal meconium extract containing substantially all target analytes present, if any, in a sample of infant meconium is provided. The target analytes are generally selected from analytes associated with the drugs of abuse and may include amphetamine, opiate, cocaine metabolite, cannabinoids, PCP, and mixtures of any of the foregoing analytes.

In accordance with the improved method, a test sample of newborn meconium suspected of containing at least one target analyte is provided. A substantially non-aqueous volatile mixture of acetonitrile and a volatile organic acid is added to the sample to form a first mixture. The first mixture is agitated for a time sufficient to extract substantially all of the target analytes present in the meconium sample without diluting the sample with water until a substantially uniform liquid homogenate is obtained. The liquid homogenate is centrifuged to form a two-phase mixture including an organic phase and a second phase. The organic phase is separated from the second phase, such as by decanting, and the separated organic phase is thereafter diluted with water to provide an aqueous organic solution suitable for solid phase column separation.

In accordance with the improved method of this invention, a single mixed mode solid phase extraction column is employed to selectively bindingly remove target analytes from the aqueous organic solution. More particularly, the solid phase extraction column includes strong cationic exchange and hydrophobic functionality. The target analytes present in the organic solution are separated by adding the organic solution to the solid phase extraction column.

Target analytes become bound to the column and other portions of the organic solution are permitted to exit the column. The column containing bound target analytes is dried. Thereafter, bound neutral and acid analytes are collected by eluting the column with a solvent reagent including a mixture of a hydrocarbon and a carboxylic acid ester into a first container to provide an acid-neutral fraction. The acid-neutral fraction is evaporated to dryness.

Thereafter, bound basic analytes are collected from the same column by eluting the column with a second solvent reagent including a polar organic solvent, an alkanol and a volatile base into a second container to provide a base fraction. The base fraction is combined with the dried acid-neutral fraction to form a combined fraction which is evaporated to dryness. The combined fraction is acidified with 1% sulfuric acid to prevent amphetamine loss, and thereafter, evaporated to dryness.

The concentrated neonatal extract product is provided by reconstituting the acidified combined fraction with a protein modified phosphate buffer at a pH of 5.0 to 8.5 to provide a concentrated neonatal extract suitable for use in qualitative immunoassay or quantitative GC/MS procedures.

DETAILED DESCRIPTION OF THE PREFERRED EMBODIMENT

Example 1

The improved meconium extraction method in accordance with the preferred embodiment of the present invention employs the following protocols:

Extraction Columns

Solid-phase extraction columns were a mixed mode moiety consisting of strong cation exchange (benzene sulfonic acid) and hydrophobic portions (C8–C12). Commercial vendors of suitable products include United Chemical Technologies (Clean Screen), Jones Chromatography (Isolute) and J. T. Baker (Narcl).

200 mg bed mass and a minimum column volume of 10 ml. were required.

The vacuum system required for solid-phase extraction consisted of a 16-place of 20-place manifold connected to a vacuum with a maximum value of 30 mm Hg.

Solvents

The following solvents and solutions were required. All were of ACS or HPLC grade:

Glacial acetic acid

Hexane

Ethyl acetate

Acetonitrile

Isopropanol

Methylene chloride

Concentrated ammonium hydroxide 0.1 M hydrochloric acid

1% sulfuric acid

Additional Requirements

A variable speed homogenizer (Omni International a balance accurate to 10 mg and a centrifuge capable of 2100 rpm were also required.

Method

1. Mix meconium sample thoroughly and weigh out an aliquot (0.5–1.0 g).
2. Add acetonitrile: acetic acid (50:50 v,v; 3mL) and homogenize at high speed until a smooth uniform homogenate is produced.
3. Centrifuge at 2100 rpm (5 minutes).
4. Decant supernatant and add deionized water (12mL). Mix and centrifuge at 2100 rpm (5 minutes).
5. Prepare solid-phase column:
   3mL methanol
   3mL deionized water
   1mL 1.93 M acetic acid Do not let the column dry out completely between each conditioning stage.

6. Add the sample and draw through the column under minimal vacuum.

7. Allow the sample to dry onto the column. Wash with:

3mL deionized water

1mL 0.1M hydrochloric acid

1mL acetonitrile/water (20:80 v,v)

8. Dry column for 5 minutes under full vacuum.

9. Place collection tubes in rack.

10. Collect acid-neutral fraction by passing hexane/ethyl acetate (50:50 v,v; 3mL) through the column.

11. Decant acid-neutrals into a cup and evaporate to dryness.

12. Wash column with 3mL methanol.

13. Place clean collection tubes in rack. Collect base fraction by passing methylene chloride:isopropanol ammonium hydroxide (78:20:2 v,v; 3mL) through column under gravity.

14. Pour bases into the corresponding dried down acid-neutral fractions.

15. Evaporate to dryness.

16. After 2 minutes of drying, add 1 drop 1% sulfuric acid to cups to prevent any amphetamine loss. Continue to evaporate to dryness.

17. Reconstitute in Abbott $AD_x$ Buffer (protein modified phosphate buffer pH 5.0–8.5) and transfer to immunoassay cups.

18. Run immunoassay screens using enzyme multiplied immunoassay technique (EMIT) or fluorescence polarization immunoassay (FPIA).

The new and improved extraction method in accordance with the present invention provided lower limit sensitivity cut-offs for the NIDA-5 panel of drugs as follows:

| | |
|---|---|
| Cocaine metabolite | 25 ng/g |
| Amphetamines | 100 ng/g |
| Opiates | 25 ng/g |
| THC netabolite | 25 ng/g |
| Phencyclidine | 25 ng/g |

In accordance with the new and improved method, a superior extraction with higher drug recovery is provided which in turn will lead to higher detection and sensitivity in quantitative and qualitative assay procedures employed using the improved neonatal meconium extracts.

The above-mentioned patent is incorporated by reference herein in its entirety.

Although the present invention has been described with reference to certain preferred embodiments, modifications or changes may be made therein by those skilled in this art without departing from the scope and spirit of the present invention as defined by the appended claims.

What is claimed is:

1. A method for preparing a concentrated neonatal meconium extract containing substantially all of at least one target analyte present, if any, in a sample of infant meconium suspected of containing said at least one target analyte, said at least one target analyte being selected from the group consisting of amphetamine, opiate, cocaine metabolite, cannabinoids, PCP and mixtures of any of the foregoing, said concentrated meconium extract being specifically intended for use in subsequent qualitative and quantitative determinations of maternal use or exposure to said at least one target analyte during pregnancy and fetal exposure to said at least one target analyte, said method comprising:

(a) providing a test sample of newborn meconium suspected of containing said at least one target analyte;

(b) adding a substantially non-aqueous volatile mixture of acetonitrile and a volatile organic acid to said sample to form a first mixture;

(c) agitating the first mixture for a time sufficient to extract substantially all of said at least one target analyte from the meconium sample, without diluting the sample with water, until a substantially uniform liquid homogenate is obtained;

(d) centrifuging the liquid homogenate to form a two-phase mixture including an organic phase and a second phase;

(e) separating the organic phase from the second phase and diluting the organic phase with water to provide an aqueous organic solution suitable for solid-phase column separation;

(f) providing a mixed-mode, solid-phase extraction column having a strong cation exchange and hydrophobic functionality;

(g) separating said at least one target analyte present in the organic solution by adding the organic solution to the solid-phase extraction column in a manner permitting any said at least one target analyte present in the organic solution to become bound to the column;

(h) drying the column;

(i) collecting any bound neutral and acid analytes by eluting the column with a first solvent reagent including a mixture of a hydrocarbon and a carboxylic acid ester into a first container to provide an acid-neutral fraction;

(j) evaporating the acid-neutral fraction to dryness;

(k) collecting any bound basic analytes from the same column by eluting the column with a second solvent reagent including a polar organic solvent, an alkanol and a volatile base into a second container to provide a base fraction;

(l) combining the base fraction with the dried acid-neutral fraction to provide a combined fraction and evaporating the combined fraction to dryness;

(m) acidifying the dried combined fraction with 1% sulfuric acid to prevent amphetamine loss and evaporating to dryness; and (n) thereafter, forming a concentrated neonatal meconium extract by reconstituting the acidified combined fraction with a protein-modified phosphate buffer at a pH of between about 5.0–8.5, suitable for use in subsequent qualitative and quantitative analytical procedures.

* * * * *